(12) United States Patent
Beebe et al.

(10) Patent No.: US 9,459,189 B2
(45) Date of Patent: Oct. 4, 2016

(54) DEVICE FOR ISOLATING A FRACTION IN A BIOLOGICAL SAMPLE

(71) Applicant: Wisconsin Alumni Research Foundation, Madison, WI (US)

(72) Inventors: David J. Beebe, Monona, WI (US); Scott M. Berry, Madison, WI (US); David J. Guckenberger, Oconomowoc, WI (US); Ben P. Casavant, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/243,086

(22) Filed: Apr. 2, 2014

(65) Prior Publication Data

US 2014/0212963 A1 Jul. 31, 2014

Related U.S. Application Data

(62) Division of application No. 13/604,192, filed on Sep. 5, 2012, now Pat. No. 8,728,411.

(51) Int. Cl.
*G01N 1/34* (2006.01)
*B01L 3/00* (2006.01)
(Continued)

(52) U.S. Cl.
CPC ........... *G01N 1/34* (2013.01); *B01L 3/502761* (2013.01); *B01L 3/502792* (2013.01); *B01L 2200/0668* (2013.01); *B01L 2200/0673* (2013.01); *B01L 2300/087* (2013.01);
(Continued)

(58) Field of Classification Search
CPC ................... B01L 2300/087; B01L 2400/043; B01L 3/502; B01L 3/50273; B01L 3/502761

USPC .......................... 210/222, 223, 695; 204/557
See application file for complete search history.

(56) References Cited

U.S. PATENT DOCUMENTS 4,855,110 A * 8/1989 Marker et al. ................ 422/547
5,279,936 A 1/1994 Vorpahl
6,117,398 A 9/2000 Bienhaus et al.
(Continued)

FOREIGN PATENT DOCUMENTS

WO 2006071770 7/2006

OTHER PUBLICATIONS

"Development of an enzymatic reaction device using magnetic bead-cluster handling", Shikida et al, J. Micromech, Microeng. 16 (2006) 1875-1883.
(Continued)

*Primary Examiner* — Jill Warden
*Assistant Examiner* — Matthew Krcha
(74) *Attorney, Agent, or Firm* — Boyle Fredrickson, S.C.

(57) ABSTRACT

A device and a method are provided for isolating a fraction in a biological sample. The fraction is bound to solid phase substrate to define a fraction-bound solid phase substrate. The device includes an input zone for receiving the biological sample therein and a second zone for receiving an isolation fluid therein. A force is provided that is generally perpendicular to gravity. The force is movable between a first position adjacent the input zone and a second position adjacent the isolation zone. The force captures the fraction-bound solid phase substrate and the fraction-bound solid phase substrate moves from the input zone to the isolation zone in response to the force moving from the first position to the second position.

18 Claims, 5 Drawing Sheets

(51) Int. Cl.
*G01N 35/00* (2006.01)
*G01N 1/40* (2006.01)

(52) U.S. Cl.
CPC ........ *B01L2400/043* (2013.01); *G01N 1/4077* (2013.01); *G01N 35/0098* (2013.01)

(56) References Cited

U.S. PATENT DOCUMENTS

| | | | |
|---|---|---|---|
| 6,506,346 B1* | 1/2003 | Monro | 422/559 |
| 8,017,340 B2 | 9/2011 | Collier et al. | |
| 8,048,633 B2 | 11/2011 | Collier et al. | |
| 8,304,188 B2 | 11/2012 | Kelso et al. | |
| 2004/0224380 A1 | 11/2004 | Chou et al. | |
| 2005/0112601 A1 | 5/2005 | Hassibi et al. | |
| 2005/0208548 A1 | 9/2005 | Block et al. | |
| 2006/0024824 A1 | 2/2006 | Woodside et al. | |
| 2007/0042396 A1 | 2/2007 | Park et al. | |
| 2008/0124779 A1 | 5/2008 | Oh et al. | |
| 2008/0226500 A1 | 9/2008 | Shikida et al. | |
| 2009/0246782 A1 | 10/2009 | Kelso et al. | |
| 2010/0291666 A1 | 11/2010 | Collier et al. | |
| 2011/0213133 A1 | 9/2011 | Beebe et al. | |
| 2012/0094275 A1 | 4/2012 | Rao et al. | |

OTHER PUBLICATIONS

"Controlled microfluidic interfaces", Atencia et al, Nature, vol. 437, Sep. 29, 2005: 648-655.

"Using wettability and interfacial tension to handle droplets of magnetic beads in a micro-chemical-analysis system", Shikida et al, Sensors and Actuators B 113 (2006) 563-569.

"Droplet-based gene expression analysis using a device with magnetic force-based-droplet-handling system", Okochi et al, Journal of Bioscience and Bioengineering, vol. 109, No. 2, 2010, 193-197.

"On-chip polymerase chain reaction microdevice employing a magnetic droplet-manipulation system", Tsuchiya et al, Sensors and Actuators B 130 (2008) 583-588.

"A novel Real Time micro PCR based Point-of-Care device for Salmonella detection in human clinical samples", Verdoy et al, Biosensors and Bioelectronics 332 (2012) 259-265.

"Forced motion of a probe particle near the colloidal glass transition", Habdas et al, Europhys. Lett., 67(3), pp. 477-583 (2004).

* cited by examiner

DEVICE FOR ISOLATING A FRACTION IN A BIOLOGICAL SAMPLE

CROSS-REFERENCE TO RELATED APPLICATION

This application is a divisional of application Ser. No. 13/604,192 filed Sep. 5, 2012.

REFERENCE TO GOVERNMENT GRANT

This invention was made with government support under W81XWH-09-1-0192 awarded by the US ARMY/MRMC. The government has certain rights in the invention.

FIELD OF THE INVENTION

The present invention relates generally to the isolation of a fraction from a biological sample, and in particular, to a device and a method for more effectively isolating cells from complex biological backgrounds so as to reduce sample loss associated therewith.

BACKGROUND AND SUMMARY OF THE INVENTION

The isolation of a specific subset of cells from a heterogeneous population of cells is necessary for a range of research and diagnostic tools. For example, isolation of circulating tumor cells (CTCs) from a buffy coat formed from a patient blood draw has shown clinical relevance. As is known, however, CTCs within the circulation of patients with metastatic cancer area very rare. More specifically, there is approximately one CTC per billion background cells. Further, the prognostically relevant bar for determining overall survival and disease-free progression of a patient is 5 CTCs per 7.5 milliliters (mLs) of whole blood. As such, CTC capture is an isolation method requiring both high sensitivity (5 cells) and high specificity (7.5 billion background cells). In addition, once captured, clinically relevant cellular analyses must be performed on the CTCs downstream of isolation.

While offering the flexibility to perform a wide range of downstream assays, macroscale methods to perform CTC isolation have been found to be unsatisfactory. More specifically, macroscale methods to isolate these types of cells often require long, expensive and laborious procedures that may result in significant sample loss due to wasteful transfer steps or centrifugation and resuspension steps. Capturing rare cells such as CTCs, which occur at frequencies on the order of 5-50 cells per 7.5 mL blood sample, is not feasible using traditional macroscale methods, as the loss of a single cell can represent up to a 20% loss of sample.

In order to overcome cell loss associated with the macroscale methods, heretofore described, microfluidic methods have arisen. Microfluidics offers novel solutions to the challenges of macroscale methods by providing a highly controlled, low-volume platform that can quickly and efficiently isolate cells. Further, microfluidic platforms offer sensitivity and specificity that is unattainable using current macroscale systems. Established microfluidic methods include functionalized micropost arrays, patterned surfaces and microfluidic systems that leverage density or other physical characteristics to isolate cells of interest from non-target cells. By way of example, Beebe et al., United States Patent Application No. 20110213133 discloses a device and a method for facilitating extraction of a fraction from a biological sample. The biological sample includes non-desired material and a fraction-bound solid phase substrate. The device includes an input zone for receiving the biological sample therein and a second zone for receiving an isolation buffer therein. An output zone receives a reagent therein. A force is movable between a first position adjacent the input zone and a second position adjacent the output zone. The force urges the fraction-bound solid phase substrate from the input zone, through the second zone and into the output zone.

While functional for its intended purpose, the device and method disclosed in the Beebe et al., '133 publication has certain limitations. For example, when the biological sample contains large particulates, debris, precipitates, or other cells that settle out of solution, the efficiency of the recovery and the overall purity of the fraction-bound solid phase substrate decreases as a result of non-desired material impeding the operational path of the fraction-bound solid phase substrate.

Therefore, it is a primary object and feature of the present invention to provide a device and a method isolating a fraction from a biological sample.

It is a further object and feature of the present invention to provide a device and a method for isolating a fraction from a biological sample that is simpler and more efficient than prior devices and methods.

It is a still further object and feature of the present invention to provide a device and a method for isolating a fraction from a biological sample without the significant sample loss associated with prior methods.

In accordance with the present invention, a device is provided for isolating a fraction in a biological sample. The fraction is bound to solid phase substrate to define a fraction-bound solid phase substrate. The device includes an input zone for receiving the biological sample therein and an isolation zone for receiving an isolation fluid therein. A force, generally perpendicular to gravity, is movable between a first position adjacent the input zone and a second position adjacent the isolation zone. The force captures the fraction-bound solid phase substrate such that the fraction-bound solid phase substrate moves from the input zone to the isolation zone in response to the force moving from the first position to the second position.

The input zone is partially defined by a lower surface lying in a first plane and wherein the device further comprising a passage having a input communicating with the input zone and an output communicating with the isolation zone. The passage is partially defined by first and second walls. The first and second side walls of the passage converge from the input to the output thereof. The passage extends along an axis. The axis is vertically spaced from the first plane. The isolation zone is partially defined by a lower surface lying in a second plane, the second plane being between the first plane and the axis. It is contemplated for the force to be a magnetic field. Further, it is contemplated for the force to move from the first position to the second position along a path transverse to gravity.

In accordance with a further aspect of the present invention, a device is provided for isolating a fraction in a biological sample. The fraction is bound to a solid phase substrate to define a fraction-bound solid phase substrate. The device includes an input zone for receiving the biological sample therein. The input zone is partially defined by a lower surface lying in a first plane. An isolation zone receives an isolation fluid therein. The isolation zone is partially defined by a lower surface lying in a second plane. A passage extends along an axis and has an input communicating with the input zone and an output communicating with the isolation zone. A force captures the fraction-bound solid phase substrate. The force is generally normal to gravity and is movable between a first position adjacent the input zone and a second position adjacent the isolation zone. The captured fraction-bound solid phase substrate moves from the input zone to the isolation zone in response to the force moving from the first position to the second position.

The passage is partially defined by first and second walls. The first and second side walls converge from the input to the output thereof. The axis of the passage is vertically spaced from the first plane and the second plane is between the first plane and the axis. It is contemplated for the force to be a magnetic field. Further, it is contemplated for the force to move from the first position to the second position along a path transverse to gravity and to the force.

In accordance with a still further aspect of the present invention, a method is provided of isolating a fraction in a biological sample. The method includes the step of providing a biological sample including a fraction-bound solid phase substrate and biological material in an input well. The input well is partially defined by a lower surface lying in a first plane. The fraction-bound solid phase substrate is captured with a force so as to maintain the fraction-bound solid phase substrate at a location above the lower surface of the input well. The biological material is allowed to settle towards the lower surface of the input well and the fraction-bound solid phase substrate is drawn into an isolation well through a passage with the force. The passage extends along an axis vertically spaced above the first plane.

It is contemplated for the force to be generally normal to gravity and to be a magnetic field. The force travels along a path to draw the fraction-bound solid phase substrate from the input well into the isolation well. The path is transverse to gravity. The passage has an input communicating with the input zone and an output communicating with the isolation zone. The passage is partially defined by first and second walls. The first and second side walls converge from the input to the output thereof. The isolation zone is partially defined by a lower surface lying in a second plane. The second plane is between the first plane and the axis.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
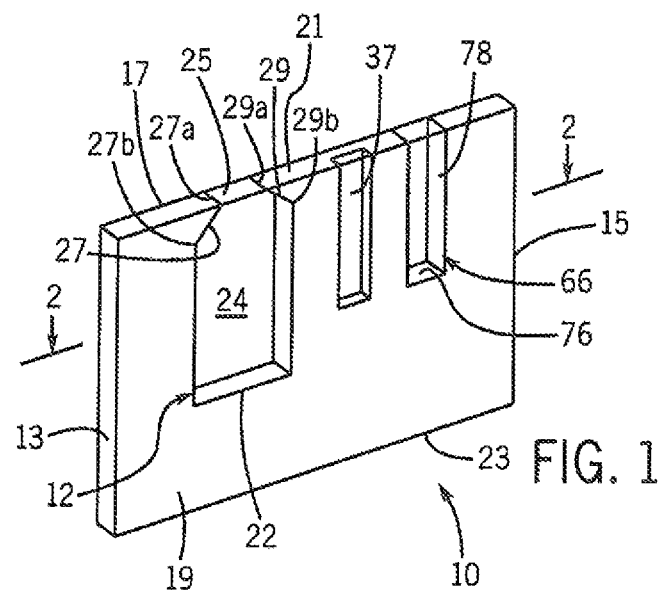
FIG. 1 is schematic, isometric view showing various wells provided in a device in accordance with the present invention in an initial configuration.
Figure 2:
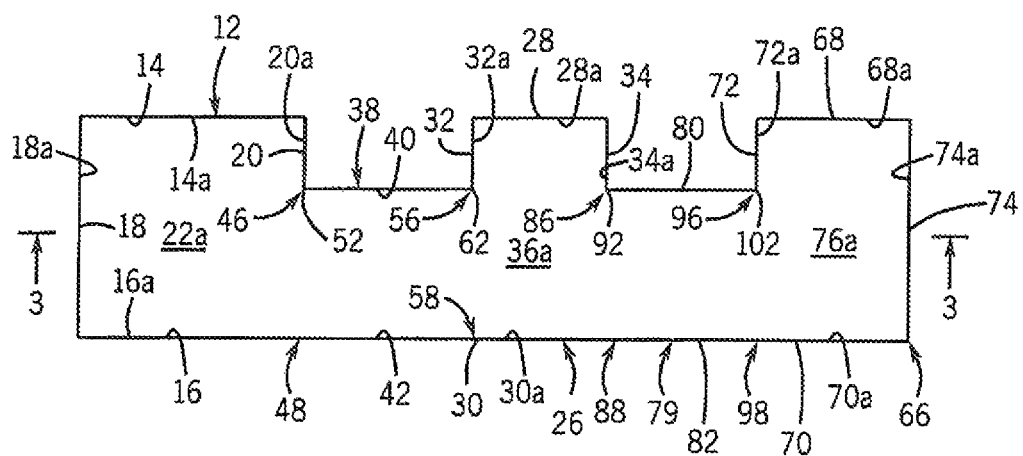
FIG. 2 is a schematic, cross-sectional view showing an outline of the various wells and channels of the device of the present invention taken along line 2-2 of FIG. 1.
Figure 3:
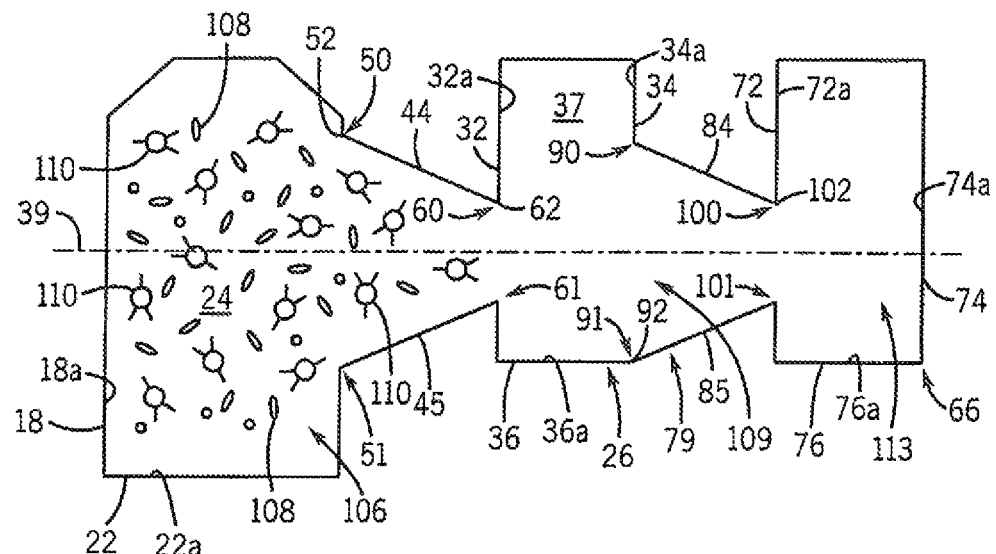
FIG. 3 is a schematic, cross-sectional view showing an outline of the various wells and channels of the device of the present invention taken along line 3-3 of FIG. 2.

Referring to FIGS. 1-6, a device for extracting and purifying a fraction, such as cells, from a complex background including non-desired cells, tissue samples and other biological materials, in accordance with the present invention, is generally designated by the reference numeral 10. Device 10 includes first and second ends 13 and 15, respectively; first and second sides 17 and 19, respectively; and upper and lower surfaces 21 and 23, respectively. Other configurations are possible without deviating from the scope of the present invention.

Device 10 further includes input zone or well 12 defined by first and second sidewalls 14 and 16, respectively, first and second end walls 18 and 20, respectively, and bottom wall 22. Input well 12 includes input 25 communicating with upper surface 21 of device 10 and being partially defined by the upper edges of sidewalls 14 and 16. Input 25 to input well 12 is further defined upper edges 27a and 29a of diverging upper walls 27 and 29. Upper edges 27a and 29a of diverging upper walls 27 and 29 are generally parallel to each other and generally perpendicular to the upper edges of first and second sidewalls 14 and 16, respectively. Lower edges 27b and 29b of upper walls 27 and 29 intersect corresponding upper edges of first and second end walls 18 and 20, respectively. In the depicted embodiment, input 25 has a generally rectangular configuration, but it can be appreciated that other configurations are possible without deviating from the scope of the present invention.

Bottom wall 22 of input well 12 lies in a first plane, for reasons hereinafter described. Inner surfaces 14a and 16a of sidewalls 14 and 16, respectively, inner surfaces 18a and 20a of first and second end walls 18 and 20, respectively, and upper surface 22a of bottom wall 22 define input cavity 24 for receiving a biological sample therein. While input well 12 has a generally rectangular configuration in the depicted embodiment, other configurations are contemplated without deviating from the scope of the present invention. It can be appreciated that a user can fill input cavity 24 with the biological sample through input 25 of input well 12.

Second well 26 is provided in device 10 downstream of input well 12. Second well 26 is defined by first and second sidewalls 28 and 30, respectively, upstream wall 32, downstream wall 34 and bottom wall 36. Bottom wall 36 of second well 26 lies in a second plane vertically spaced above the first plane. Inner surfaces 28a and 30a of sidewalls 28 and 30, respectively, inner surface 32a of upstream wall 32, inner surface 34a of downstream wall 34, and upper surface 36a of bottom wall 36 define second cavity 37 for receiving a predetermined fluid therein, e.g. isolation buffer as hereinafter described. Again, although second well 26 has a generally rectangular configuration in the depicted embodiment, other configurations are contemplated without deviating from the scope of the present invention.

Input well 12 and second well 26 are interconnected by first passage 38. First channel 38 extends along an axis 39 which is vertically spaced from and above the first and second planes. First channel 38 is defined by first and second sidewalls 40 and 42, respectively, upper wall 44 and bottom wall 45. Input ends 46 and 48 of first and second sidewalls 40 and 42, respectively, of first channel 38 and input ends 50 and 51 of upper and bottom walls 44 and 45, respectively, of input channel 38 intersect end wall 20 of input well 12 so as to define input 52 to first channel 38. Output ends 56 and 58 of first and second sidewalls 40 and 42, respectively, of first channel 38 and output ends 60 and 61 of upper and bottom walls 44 and 45, respectively, of first channel 38 intersect upstream wall 32 of second well 26 so as to define output 62 of first channel 38. First and second sidewalls 40 and 42, respectively, of first channel 38 are generally parallel to each other, FIG. 2. As best seen in FIGS. 1 and 3-6, upper and bottom walls 44 and 45, respectively, respectively, of first channel 38 converge towards each other from input 52 to output 62, for reasons hereinafter described.

Device 10 further includes third zone or well 66 downstream of second well 26 and being defined by first and second sidewalls 68 and 70, respectively, upstream wall 72, downstream wall 74 and bottom wall 76. Bottom wall 76 of third well 66 lies in the second plane vertically spaced above the first plane. Inner surfaces 68a and 70a of sidewalls 68 and 70, respectively, inner surface 72a of upstream wall 72, inner surface 74a of downstream wall 74, and upper surface 76a of bottom wall 76 define output cavity 78 for receiving a predetermined fluid, e.g. a reagent, therein for reasons hereinafter described. Again, third well 66 has a generally rectangular configuration in the depicted embodiment. However, other configurations are contemplated without deviating from the scope of the present invention.

Third well 66 and second well 26 are interconnected by second channel 79. Second channel 79 extends along axis 39 and is defined by first and second sidewalls 80 and 82, respectively, upper wall 84 and bottom wall 85. Input ends 86 and 88 of first and sidewalls 80 and 82, respectively, of second channel 79 and input ends 90 and 91 of upper and bottom walls 84 and 85, respectively, of second channel 79 intersect downstream wall 34 of second well 26 so as to define input 92 to second channel 79. Output ends 96 and 98 of first and second sidewalls 80 and 82, respectively, of second channel 79 and output ends 100 and 101 of upper and bottom walls 84 and 85, respectively, of second channel 79 intersect upstream wall 72 of third well 66 so as to define output 102 of second channel 79. First and second sidewalls 80 and 82, respectively, of second channel 79 are generally parallel to each other, FIG. 2, As best seen in FIGS. 1 and 3-6, upper and bottom walls 84 and 85, respectively, of second channel 79 converge towards each other from input 92 to output 102, for reasons hereinafter described.

In operation, it is intended to utilize device 10 to extract a fraction, such as a desired cell, nucleic acids, and/or proteins, from biological sample 106. As is known, biological sample 106 may include non-desired material 108 such as lysate, bodily fluids, forensic samples, and/or biological contaminations. In order to prepare biological sample 106 for extraction of the fraction, an appropriate reagent is added to biological sample 106 and mixed such that fraction binds to a solid phase substrate in the reagent to form fraction-bound solid phase substrate 110. It is contemplated for the solid phase substrate to be attracted to a corresponding force. For example, the solid phase substrate may be a paramagnetic material attracted to a corresponding magnetic field. Other non-magnetic mechanisms such as ultrasonic actuation or the like are contemplated as being within the scope of the present invention. Once mixed with the reagent, biological sample 106 including fraction-bound solid phase substrate 110 is deposited into input cavity 24 through input 25 of input well 12. It is noted that the reduced cross-sectional area of input 25 to input well 12 pins biological sample 106 within input cavity 24 such that invasion of device 10 will not result in biological sample 106 spilling out of input well 12 through input 25 thereof. Hence, it can be appreciated that device 10 may be rotated and for inverted to facilitate the mixing of biological sample 106 and the reagent in input cavity 24 of input well 12 or maintain fraction-bound solid phase substrate 110 in suspension.

In addition to depositing biological sample 106 in input cavity 24 of input well 12, isolation buffer 109, such as oil or wax, is deposited in second cavity 37 of second well 26; and a desired reagent 113 is deposited in third cavity 78 of third well 66. Device 10 of the present invention relies upon the dominance of surface tension over gravity at the microscale to establish "virtual walls" between each fluid interface. This dominance of surface tension enables the side-by-side loading of fluids in the devices that is not possible on the macroscale. This phenomenon is quantified by the dimensionless Bond number:

$$Bo = \rho g L 2/\gamma \qquad \text{Equation (1)}$$

wherein: Bo is the Bond number; ρ is the density of a fluid; g is the acceleration of gravity; L is a characteristic length scale of the device; and γ is the surface energy of fluid.

A Bond number (Bo) less than 1 indicates a system in which surface tension forces are sufficiently large to marginalize the effects of gravity. For larger Bond number (Bo) devices, gravity dominance mandates positioning of the denser biological sample in input well 12 and reagent in third well 66 below the isolation buffer in second well 26, constraining device geometry into a three-dimensional architecture. Because Bond number (Bo) scales with the square of the characteristic length scale of the device ($L^2$), a reduction in device dimensions rapidly reduces the Bond number (Bo) into the surface tension-dominant regime. Microfluidic constrictions with very small characteristic length scales selectively impede liquid motion, enabling serial loading of all three device fluids the biological sample, the isolation buffer and the reagent) into their respective wells (input well 12, second well 26 and third well 66, respectively) without intermixing or density-driven stratification. Hence, the reliance upon the dominance of surface tension, allow for the planarization of the layout of the devices of the present invention which, in turn, simplifies both device fabrication and operation while also enabling high-throughput arrays in well plate-like configurations.

In view of the foregoing, it is noted that the cross-sectional area of input 52 to first channel 38 is greater than the cross-sectional area of output 62 of first channel 38. As a result, biological sample 106 flows into first channel 38 through input 52 thereof. However, the surface tension of isolation buffer 109 in second cavity 37 of second well 26 at output 62 of first channel 38 prevents biological sample 106 from flowing into second cavity 37 of second well 26 through output 62 of first channel 38. Likewise, the surface tension of reagent 113 in third cavity 78 of third well 66 at output 102 of second channel 79 prevents isolation buffer 109 from flowing into third cavity 78 of third well 66 at output 102 of second channel 79.

Figure 4:
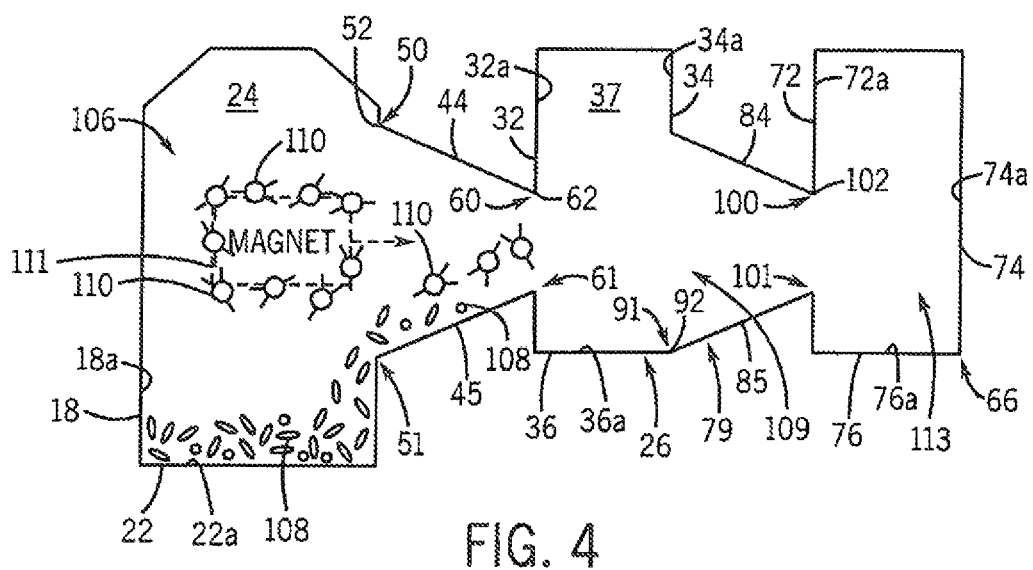
FIG. 4 is a schematic, cross-sectional view of the device, similar to FIG. 3, showing an initial step of the methodology of the present invention.

In order to extract fraction-bound solid phase substrate 110 from biological sample 106, a force to which the solid phase substrate is attracted, such as magnet 111, is positioned adjacent second sidewall 19 of device 10 at a location aligned with second sidewall 16 of input well 12 in a plane containing axis 39 of first and second channels 38 and 79, respectively, FIG. 4. As heretofore described, it is contemplated for the solid phase substrate to be a paramagnetic material attracted to a corresponding magnetic field generated by magnet 111. As such, fraction-bound solid phase substrate 110 are drawn towards axis 39 through first and second channels 38 and 79, respectively, thereby suspending fraction-bound solid phase substrate 110 above bottom wall 22 of input well 12. With fraction-bound solid phase substrate 110 suspended above bottom wall 22 of input well 12, non-desired material 108 in biological sample 106 settles passively to bottom wall 22 of input well 12 of device 10. Thereafter, magnet 111 is moved adjacent second sidewall 19 of device 10 along an axis generally parallel to axis 39. More specifically, magnet 111 moves from the location aligned with second sidewall 16 of input well 12 to a location aligned with second sidewall 42 of first channel 38 such that fraction-bound solid phase substrate 110 are drawn into first channel 38 through input 52 thereof. It can be appreciate that with fraction-bound solid phase substrate 110 suspended above bottom wall 22 of input well 12, fraction-bound solid phase substrate 110 is free to travel from input well 12 to first channel 38 without interference from non-desired material 108 in biological sample 106 that previously settled to bottom wall 22 of input well 12 of device 10, thereby allowing for a higher percentage of the fraction-bound solid phase substrate 110 to be drawn through device 10 than prior methods.

Figure 5:
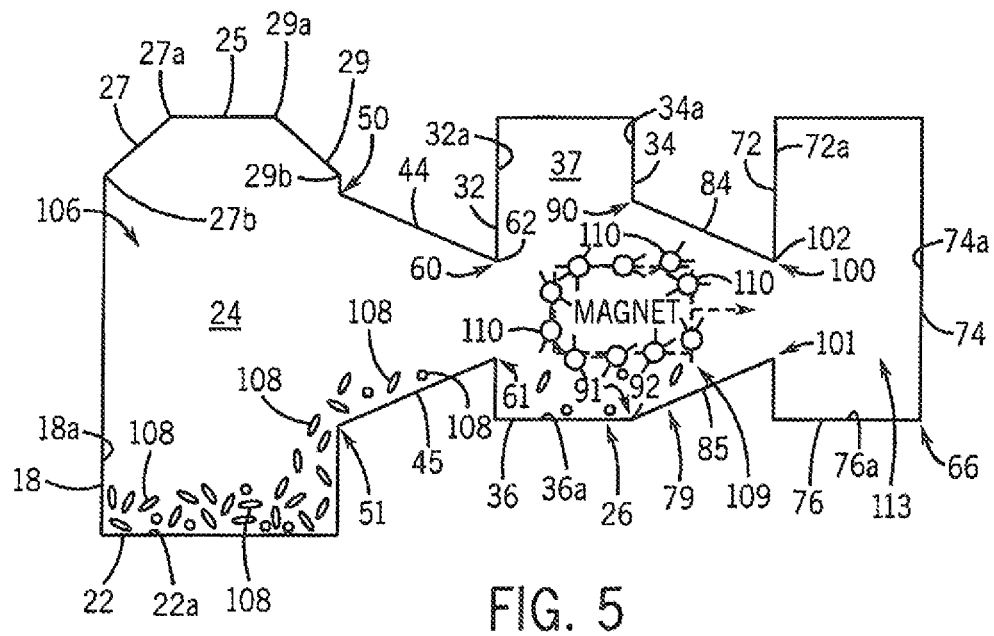
FIG. 5 is a schematic, cross-sectional view of the device, similar to FIG. 3, showing a second step of the methodology of the present invention.

Magnet 111 is then moved axially along second sidewall 19 of device 10 from the location aligned with second sidewall 42 of first channel 38 to a location, aligned with second sideman 30 of second well 26 such that fraction-bound solid phase substrate 110 is drawn along axis 39 into second well 26 through output 62 of first channel 38, FIG. 5. As fraction-bound solid phase substrate 110 is drawn into second well 26, fraction-bound solid phase substrate 110 is suspended above bottom wall 36. With fraction-bound solid phase substrate 110 suspended above bottom wall 36 of second well 26, any non-desired material 108 in biological sample 106 inadvertently drawn into second well 26 with fraction-bound solid phase substrate 110 is then allowed to settle passively to bottom wall 36 of second well 26 of device 10.

Once any non-desired material 108 in biological sample 106 inadvertently drawn into second well 26 with fraction-bound solid phase substrate 110 is allowed to settle passively to bottom wall 36 of second well 26 of device 10, magnet 111 is moved axially along second sidewall 19 of device 10 from the location aligned with second sidewall 30 of second well 26 to a location aligned with second sidewall 82 of second channel 79 such that fraction-bound solid phase substrate 110 is drawn into second channel 79 through input. 92 thereof. It can be appreciate that with fraction-bound solid phase substrate 110 suspended above bottom wall 36 of second well 12, fraction-bound solid phase substrate 110 are free to travel from second well 26 to second channel 79 without interference from non-desired material 108 in biological sample 106 that previously settled to bottom wall 36 of second well 26 of device 10.

Figure 6:
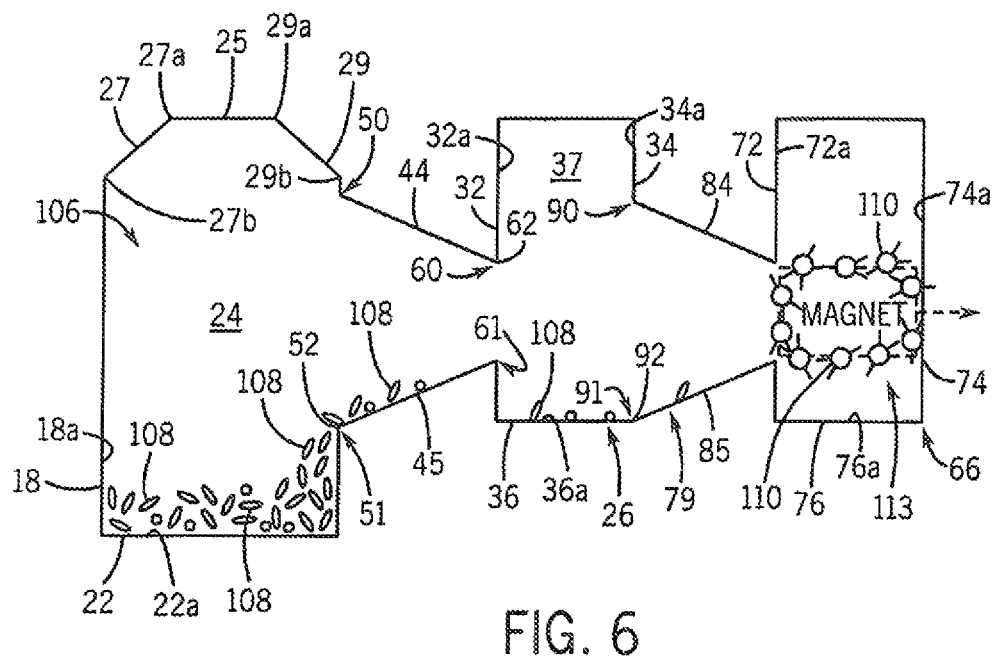
FIG. 6 is a schematic, cross-sectional view of the device, similar to FIG. 3, showing a third step of the methodology of the present invention.
Figure 7:
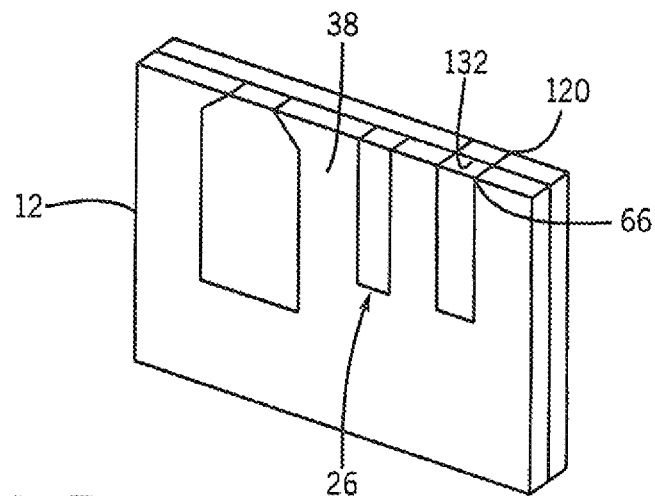
FIG. 7 is an isometric view of an alternate embodiment of the device of the present invention.
Figure 8:
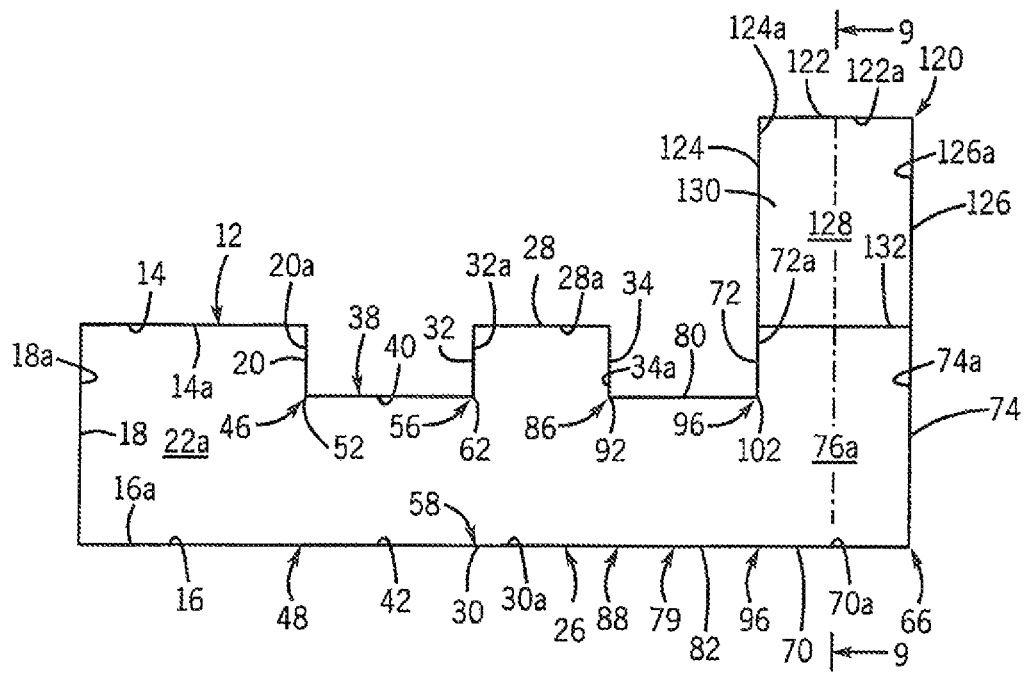
FIG. 8 is a schematic, cross-sectional view of the device of the present invention taken along line 8-8 of FIG. 7.
Figure 9:
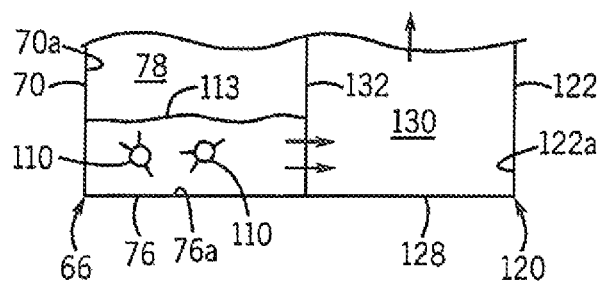
FIG. 9 is a schematic, cross-sectional view of the device taken along line 9-9 of FIG. 8 showing an additional step the methodology of the present invention.
Figure 10:
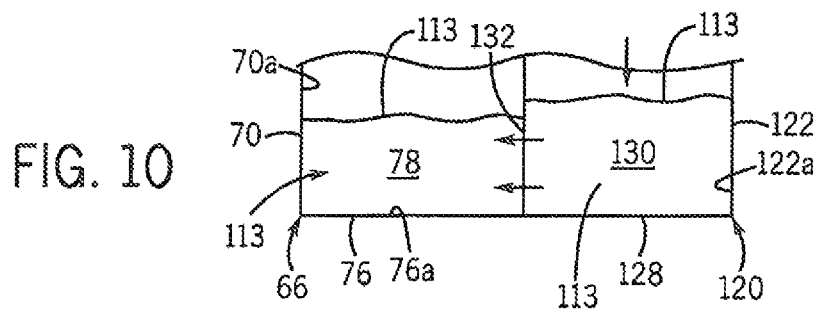
FIG. 10 is a schematic, cross-sectional view of the device, similar to FIG. 9, showing a still further step of the methodology of the present invention.

Magnet 111 is then moved axially along second sidewall 19 of device 10 from the location aligned with second sidewall 82 of second channel 79 to a location aligned with second sidewall 70 of third well 66 such that fraction-bound solid phase substrate 110 are drawn along axis 39 into third well 66 through output 102 of second channel 79, FIG. 6. As fraction-bound solid phase substrate 110 are drawn into third well 66, fraction-bound solid phase substrate 110 are suspended above bottom wall 76. With fraction-bound solid phase substrate 110 suspended above bottom wall 76 of third well 66, any non-desired material 108 in biological sample 106 inadvertently drawn into third well 66 with fraction-bound solid phase substrate 110, if any, are then allowed to settle passively to bottom wall 76 of third well 66 of device 10.

As previously noted, the surface tension of isolation buffer 109 in second cavity 37 of second well 26 at output 62 of first channel 38 prevents biological sample 106 from flowing into second cavity 37 of second well 26 through output 62 of first channel 38 and the surface tension of reagent 113 in third cavity 78 of thud well 66 at output 102 of second channel 79 prevents isolation buffer 109 from flowing into third cavity 78 of third well 66 at output 102 of second channel 79. It can be appreciated that as fraction-bound solid phase substrate 110 passes through second well 26 and second channel 79, fraction-bound solid phase substrate 110 are washed by isolation buffer 109 therein, thereby effectively isolating fraction-bound solid phase substrate 110 from the remainder of biological sample 106. With fraction-bound solid phase substrate 110 isolated from the remainder of biological sample 106 in third well 66, fraction-bound solid phase substrate 110 may be treated in third well 66 by reagent 113 contained therein, as desired by a user. Alternatively, it is contemplated for reagent 113 in third well 66 to be an elution buffer such that the fraction bound to the solid phase substrate may be extracted therefrom. In addition, it can be appreciated that third well 66 may be operatively connected to additional downstream components for further processing of fraction-bound solid phase substrate 110.

As described, the methodology of the present invention does not require any electronic equipment such as centrifuges, rockers/shakers, or incubators, while consuming only minimal volumes of reagents in the three wells. It can also be appreciated that the simplicity of device 10 allows for it to be easily reconfigured to form a mating relationship with the input/output requirements of upstream and downstream components.

It is also noted that it contemplated as being within the scope of the present invention to provide an array of the devices as heretofore described in combination with an array of permanent magnets in a 1:1 ratio. Alternatively, an array of electromagnets may be utilized to provide adaptable and programmable movement of the magnetic field with no moving parts. Also, bar magnets that simultaneously move the solid phases through multiple independent wells may be used. It can be further appreciated that either the magnet 111 or the device 10 of the present invention can be the movable part to effectuate the methodology of the present invention. Additionally, it can be appreciated that physical alignment constructs ensure precise alignment between the device of the present invention and the magnetic apparatus.

Referring to FIGS. 7-10, in order to provide for the simple media replacement of reagent 113 in third cavity 78 of third well 66, it is contemplated to position replacement well 120 adjacent third well 66. More specifically, replacement well 120 is defined by first sidewall 122, first and second end walls 124 and 126, respectively, and bottom wall 128. Inner surface 122a of first sidewall 122, inner surfaces 124a and 126a of first and second end walls 124 and 126, respectively, and the upper surface of bottom wall 128 define replacement cavity 130 for receiving a replacement media therein. While replacement well 120 has a generally rectangular configuration in the depicted embodiment, other configurations are contemplated without deviating from the scope of the present invention. As described, it is intended for first and second end walls 124 and 126, respectively, and bottom wall 128 of replacement well 120 to be generally co-planar with corresponding upstream wall 72, downstream wall 74 and bottom wall 76 of third well 66, FIG. 8. Micropourous membrane 132 is positioned between replacement cavity 130 and third cavity 78 to separate the cavities.

In operation, biological sample 106 is deposited in input cavity 24 of input well 12; isolation buffer 109, such as oil or wax, is deposited in second cavity 37 of second well 26; and a desired reagent 113 is deposited in third cavity 78 of third well 66, as heretofore described. Reagent 113 is also deposited in replacement cavity 130 of replacement well 120. Thereafter, fraction-bound solid phase substrate 110 are drawn into third well 66, as heretofore described. In order to replace reagent 113 in third cavity 78 of third well 66, reagent 113 is aspirated from replacement cavity 128, FIG. 9. During aspiration, reagent 113 in third cavity 78 flows through micropourous membrane 130 and into replacement cavity 128, thereby allowing both replacement cavity 128 and third cavity 78 to be emptied. It can be appreciated that micropourous membrane 130 prevents fraction-bound solid phase substrate 110 (as well as any cells, beads, analyte or the like) in third cavity 78 from flowing into replacement cavity 128 and being aspirated. This, in turn, allows for the replacement of reagent 113 in third cavity 78 without ever have to remove or centrifuge fraction-bound solid phase substrate 110 from reagent 113 in third cavity 78. Once all of reagent 113 is removed from third cavity, new media may be added to replacement cavity 128. The new media flows through micropourous membrane 132 and fills third cavity 78. These steps can be repeated multiple times, thereby allowing staining, permeabalization, fixation, etc. to take place in third cavity 78 without ever removing fraction-bound solid phase substrate 110 or the like from device 10. As a result, the loss of any fraction of interest due to the transfer of such fraction from device 10 to alternative device, e.g. a test tube, is eliminated.

Various modes of carrying out the invention are contemplated as being within the scope of the following claims particularly pointing out and distinctly claiming the subject matter, which is regarded as the invention.

We claim:

1. A device for isolating a fraction in a biological sample, the fraction being bound to solid phase substrate to define a fraction-bound solid phase substrate, comprising:
   an input zone for receiving the biological sample therein, the input zone partially defined by first and second spaced end walls and a lower surface therebetween;
   an isolation zone for receiving an isolation fluid therein, the biological sample and the isolation fluid having an interface with a surface tension;
   a passage having an input communicating with the input zone and an output communicating with the isolation zone, the input of the passage partially defined by an upper wall and a lower wall intersecting the second end wall of the input zone at an edge lying in a horizontal plane vertically spaced from the lower surface of the input zone such that a portion of the input zone lies between the horizontal plane and lower surface of the input zone; and
   a force generator configured to generate a force working against gravity, the force being movable by the force generator between a first position adjacent the input zone and a second position adjacent the isolation zone;

wherein:
   the surface tension of the interface retaining the biological sample in the input zone and the isolation fluid in the isolation zone;
   the force captures the fraction-bound solid phase substrate and suspends the fraction-bound solid phase substrate within the input zone with the force in the first position; and
   the fraction-bound solid phase substrate moves from the input zone to the isolation zone in response to the force moving from the first position to the second position.

2. The device of claim 1 wherein the upper and lower walls of the passage converge from the input to the output thereof.

3. The device of claim 1 wherein the passage extends along an axis, the axis being vertically spaced from the lower surface of the input zone.

4. The device of claim 3 wherein the isolation zone is partially defined by a lower surface lying in a second plane, the second plane being between the lower surface of the input zone and the axis.

5. The device of claim 1 wherein the force generator is configured to generate a magnetic field as the force.

6. The device of claim 1 wherein the force generator is configured to move the force between the first position to the second position along a linear path transverse to gravity.

7. The device of claim 1 further comprising:
   a reagent zone downstream of and in communication with the isolation zone, the reagent zone receiving a reagent therein;
   a replacement zone in fluid communication with the reagent zone; and
   a microporous membrane separating the reagent zone and the replacement zone.

8. The device of claim 1 wherein the biological sample is retained in the input zone by surface tension.

9. The device of claim 1 wherein the input zone has a cross-sectional area and an input having a cross-sectional area and wherein the cross-sectional area of the input zone is greater than the cross-sectional area of the input to the input zone.

10. A device for isolating a fraction in a biological sample, the fraction being bound to solid phase substrate to define a fraction-bound solid phase substrate, the device comprising:
   an input zone for receiving the biological sample therein, the input zone partially defined by first and second spaced end walls and a lower surface therebetween lying in a first plane;
   a second zone for receiving a fluid therein, the second zone partially defined by a lower surface;
   a passage extending along an axis and having an input communicating with the input zone and an output communicating with the second zone, the input of the passage partially defined by a lower wall intersecting the second end wall of the input zone at a location vertically spaced from the lower surface of the input zone and lying in a second plane such that a lower portion of the input zone lies between the first and second planes; and
   a force generator configured to generate a force for capturing the fraction-bound solid phase substrate and suspending the fraction-bound solid phase substrate within the input zone, the force working against gravity and being movable by the force generator between a first position adjacent the input zone and a second position adjacent the second zone;

wherein:
the biological sample and the fluid having an interface with a surface tension, the surface tension of the interface retaining the biological sample in the passage and the fluid in the second zone; and
the captured fraction-bound solid phase substrate moves from the input zone to the second zone in response to the force moving from the first position to the second position.

11. The device of claim 10 wherein the passage is partially defined by an upper wall and the lower wall, the upper and lower walls converging from the input to the output thereof.

12. The device of claim 10 wherein the axis is vertically spaced from the first plane.

13. The device of claim 12 wherein the lower surface of the second zone lies in a third plane, the third plane being between the first plane and the axis.

14. The device of claim 10 wherein the force generator is configured to generate a magnetic field as the force.

15. The device of claim 10 wherein the force generator is configured to move the force between the first position to the second position along a linear path transverse to gravity.

16. The device of claim 10 further comprising:
a third zone downstream of and in communication with the second zone, the third zone receiving a second fluid therein;
a replacement zone in fluid communication with the third zone; and
a micropourous membrane separating the third zone and the replacement zone.

17. The device of claim 10 wherein the biological sample is retained in the input zone by surface tension.

18. The device of claim 10 wherein the input zone has a cross-sectional area and an input having a cross-sectional area and wherein the cross-sectional area of the input zone is greater than the cross-sectional area of the input to the input zone.

* * * * *